US009513256B2

(12) United States Patent
Taylor

(10) Patent No.: US 9,513,256 B2
(45) Date of Patent: Dec. 6, 2016

(54) ION MOBILITY SPECTROMETER WHICH CONTROLS CARRIER GAS FLOW TO IMPROVE DETECTION

(71) Applicant: Smiths Detection-Watford Limited, Bushey, Watford, Hertfordshire (GB)

(72) Inventor: Stephen John Taylor, Hyde Heath (GB)

(73) Assignee: Smiths Detection-Watford Limited, Watford, Hertfordshire (GB)

( * ) Notice: Subject to any disclaimer, the term of this patent is extended or adjusted under 35 U.S.C. 154(b) by 243 days.

(21) Appl. No.: 14/082,827

(22) Filed: Nov. 18, 2013

(65) Prior Publication Data

US 2014/0087477 A1    Mar. 27, 2014

Related U.S. Application Data

(62) Division of application No. 12/521,537, filed as application No. PCT/GB2007/004705 on Dec. 10, 2007, now Pat. No. 8,668,870.

(30) Foreign Application Priority Data

Dec. 20, 2006 (GB) .................................. 0625479.1

(51) Int. Cl.
*G01N 27/62* (2006.01)
*H01J 49/04* (2006.01)

(52) U.S. Cl.
CPC .......... *G01N 27/622* (2013.01); *H01J 49/0422* (2013.01); *Y10T 436/25875* (2015.01)

(58) Field of Classification Search
CPC .............. G01N 27/622; H01J 49/0422; Y10T 436/25875
See application file for complete search history.

(56) References Cited

U.S. PATENT DOCUMENTS

| 3,107,966 | A |   | 10/1963 | Bonhomme |
| 3,461,285 | A |   | 8/1969 | Werner et al. |
| 3,470,527 | A |   | 9/1969 | Bonhomme |
| 3,787,681 | A |   | 1/1974 | Brunnee et al. |
| 4,378,499 | A |   | 3/1983 | Spangler et al. |
| 4,551,624 | A |   | 11/1985 | Spangler et al. |
| 5,071,771 | A | * | 12/1991 | Barbour ............... G01N 33/46 250/282 |
| 5,083,019 | A |   | 1/1992 | Spangler |
| 5,227,628 | A |   | 7/1993 | Turner |
| 5,304,797 | A |   | 4/1994 | Irie et al. |
| 5,574,277 | A |   | 11/1996 | Taylor |
| 5,723,861 | A |   | 3/1998 | Carnahan et al. |
| 5,834,771 | A | * | 11/1998 | Yoon ................... G01N 27/622 250/286 |
| 5,854,431 | A |   | 12/1998 | Linker et al. |
| 5,952,652 | A |   | 9/1999 | Taylor et al. |
| 6,051,832 | A |   | 4/2000 | Bradshaw |
| 6,073,498 | A |   | 6/2000 | Taylor |
| 6,102,746 | A |   | 8/2000 | Nania et al. |
| 6,225,623 | B1 |   | 5/2001 | Turner et al. |
| 6,239,428 | B1 |   | 5/2001 | Kunz |
| 6,442,997 | B1 |   | 9/2002 | Megerle |
| 6,459,079 | B1 |   | 10/2002 | Machlinski et al. |
| 6,481,263 | B1 |   | 11/2002 | Haley |
| 6,495,824 | B1 |   | 12/2002 | Atkinson |
| 6,502,470 | B1 |   | 1/2003 | Taylor et al. |
| 6,523,393 | B1 |   | 2/2003 | Linker et al. |
| 6,825,460 | B2 |   | 11/2004 | Breach et al. |
| 7,098,449 | B1 |   | 8/2006 | Miller et al. |
| 7,118,712 | B1 |   | 10/2006 | Manginell |
| 7,311,566 | B2 |   | 12/2007 | Dent |
| 2002/0150923 | A1 |   | 10/2002 | Malik |
| 2004/0259265 | A1 |   | 12/2004 | Bonne |
| 2005/0017163 | A1 |   | 1/2005 | Miller et al. |
| 2005/0095722 | A1 |   | 5/2005 | McGill et al. |
| 2005/0161596 | A1 |   | 7/2005 | Guevremont et al. |
| 2005/0178975 | A1 |   | 8/2005 | Glukhoy |
| 2005/0253061 | A1 |   | 11/2005 | Cameron et al. |
| 2006/0249673 | A1 |   | 11/2006 | Breach et al. |

FOREIGN PATENT DOCUMENTS

| EP | 0135747 | 4/1985 |
| GB | 2323165 | 9/1998 |
| WO | 199301485 | 1/1993 |
| WO | 9322033 | 11/1993 |
| WO | 199921212 | 4/1999 |
| WO | 0079261 | 12/2000 |
| WO | 0195999 | 12/2001 |
| WO | 2002078047 | 10/2002 |
| WO | 2004012231 | 2/2004 |
| WO | 2006046077 | 5/2006 |
| WO | 2008035095 | 3/2008 |

OTHER PUBLICATIONS

Tian, Wei-Cheng et al. "Multiple-stage microfabricated preconcentrator-focuser for micro gas chromatography system." Journal of Microelectromechnical Systems (2005) 14 498-507.*

* cited by examiner

*Primary Examiner* — Christopher A Hixson
(74) *Attorney, Agent, or Firm* — Reinhart Boerner Van Deuren s.c.

(57) ABSTRACT

IMS apparatus has an inlet with a preconcentrator opening into a reaction region where analyte molecules are ionized and passed via a shutter to a drift region for collection and analysis. A pump and filter arrangement supplies a flushing flow of clean gas to the housing in opposition to ion flow. A pressure pulser connects with the housing and is momentarily switched to cause a short drop in pressure, in the housing to draw in a bolus of analyte sample from the preconcentrator. Just prior to admitting a bolus of sample, the pump is turned off so that the flushing flow drops substantially to zero, thereby prolonging the time the analyte molecules spend in the reaction region.

20 Claims, 1 Drawing Sheet

ION MOBILITY SPECTROMETER WHICH CONTROLS CARRIER GAS FLOW TO IMPROVE DETECTION

CROSS-REFERENCE TO RELATED PATENT APPLICATIONS

This patent application is a division of U.S. patent application Ser. No. 12/521,537, filed on Jun. 26, 2009, entitled "Ion Mobility Spectrometer Which Controls Carrier Gas Flow to Improve Detection," now U.S. Pat. No. 8,668,870, granted on Mar. 11, 2014, which is a U.S. National Stage patent application under 35 U.S.C. Section 371 of PCT International Patent Application No. PCT/GB2007/004705, filed on Dec. 10, 2007, which in turn claims priority of Great Britain Patent Application No. 0625479.1, filed on Dec. 20, 2006, all of which are assigned to the assignee of the present patent application and all of which are hereby incorporated herein by reference in their entirety.

This patent application is also related to two issued patents and one other pending patent applications, namely U.S. Pat. No. 8,022,360, granted Sep. 20, 2011, entitled "Gas Preconcentrator for Detection Apparatus;" U.S. Pat. No. 8,158,933, granted Apr. 12, 2012, entitled "Detector Apparatus and Preconcentrators;" and U.S. patent application Ser. No. 12/521,542, filed on Jun. 26, 2009, entitled "Detection Apparatus;" all three of which are assigned to the assignee of the present patent application, which two patents and one patent application are hereby incorporated herein by reference.

BACKGROUND OF THE INVENTION

Field of the Invention

This invention relates to detection apparatus of the kind including a reaction region and an analysis region where ion species produced in the reaction region are detected, and an arrangement for supplying a flow of clean gas through the reaction region.

Ion mobility spectrometers or IMS apparatus are often used to detect substances such as explosives, drugs, blister and nerve agents, or the like. An IMS apparatus typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, UV source, or by corona discharge, and are admitted into the drift region of the cell by an electrostatic gate at one end. The ionized molecules drift to the opposite end of the cell at a speed dependent on the mobility of the ions. By measuring the time of flight along the cell, it is possible to identify the ions. In conventional IMS apparatus, clean dry gas flows continuously through the reaction or ionization region. This arrangement allows for continuous sampling and short recovery times. Where the sample analyte is only present in small concentrations in the sample gas, there can be a relatively low signal-to-noise ratio and this can make reliable detection very difficult.

It is accordingly desirable to provide alternative detection apparatus and methods of operation.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

According to one aspect of the present invention there is provided a detection apparatus of the above-specified kind, characterized in that the detection apparatus includes an arrangement for momentarily admitting an analyte gas or vapor to the reaction region, that the supply arrangement is arranged so as to reduce the flow of clean gas through the reaction region substantially to zero just prior to admitting the analyte gas or vapor to the reaction region such that the residence time of the analyte gas or vapor in the reaction region is increased, and that the supply arrangement is arranged subsequently to increase the flow of clean gas through the reaction region.

The arrangement for momentarily admitting the analyte gas or vapor preferably includes a pressure pulser arranged to reduce pressure in the detection apparatus momentarily. The detection apparatus may have an inlet arrangement including a preconcentrator. The arrangement for flowing clean gas through the reaction region may be arranged and configured to flow the clean gas along substantially the length of the detection apparatus. Alternatively, the arrangement for flowing clean gas through the reaction region may include a first gas flow circuit connected between an end of the detection apparatus remote from its inlet and an end of the reaction region remote from the inlet and the detection apparatus may include a secondary circuit extending from the first circuit to an end of the reaction region adjacent the inlet, with the secondary circuit being closed when a sample is to be admitted. The detection apparatus may be an ion mobility spectrometer.

In a method embodiment used in conjunction with a detection apparatus having a reaction region arranged to provide ions to an analysis region where ion species produced in the reaction region are detected, the method includes: selectively operating a gas flow system to supply a flow of clean gas through the reaction region; momentarily admitting an analyte gas or vapor to the reaction region while reducing the flow of clean gas through the reaction region substantially to zero just prior to momentarily admitting the analyte gas or vapor to the reaction region such that the residence time of the analyte gas or vapor in the reaction region is increased; and subsequently increasing the flow of clean gas through the reaction region.

In a method of detecting substances, the method includes: admitting a sample of a substance into a reaction chamber; flowing a gas through the reaction chamber; producing ions from the sample; passing ions from the reaction chamber to a collector for detection; and periodically reducing the flow of gas through the reaction chamber thereby to prolong the time during which the sample is present in the reaction chamber.

In another method embodiment used in conjunction with a detection apparatus having a first end at which an analyte gas or vapor will be admitted to the housing and a second end opposite the first end, the method includes: selectively admitting an analyte gas or vapor to a reaction region located in the detection apparatus adjacent the first end thereof, a drift region being located in the detection apparatus between the reaction region and the second end of the detection apparatus; selectively operating a gas flow system to supply a flow of clean gas at least through the reaction region; coordinating the operation of the admitting step and the operating step to operate the gas flow system to reduce the flow of clean gas through the reaction region substantially immediately prior to admitting the analyte gas or vapor to the reaction region such that the residence time of the analyte gas or vapor in the reaction region may be increased; and subsequently increasing the flow of clean gas through the reaction region.

The ions are preferably passed from the reaction chamber to the collector via a drift region having a voltage gradient along its length.

DESCRIPTION OF THE DRAWINGS

An IMS apparatus that is constructed and operated according to the present invention will now be described, by way of example, with reference to the accompanying drawings, in which.

DETAILED DESCRIPTION OF THE PREFERRED EMBODIMENT

Figure 1:
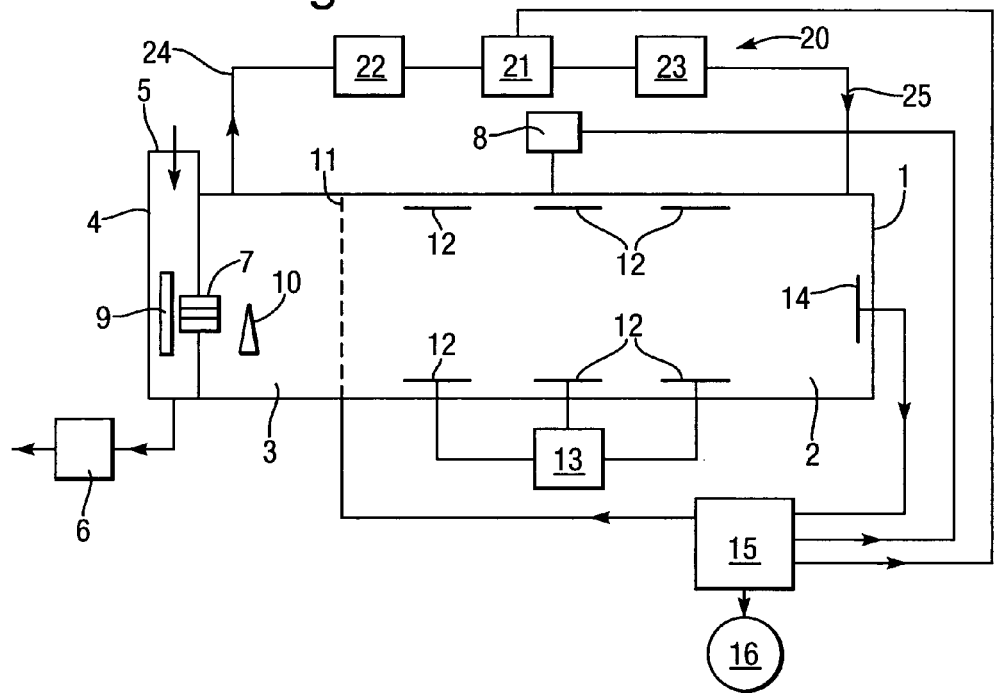
FIG. 1 shows the detection apparatus schematically.

With reference first to FIG. 1, the apparatus takes the form of an ion mobility spectrometer ("IMS") having a generally tubular housing 1 with an analysis or drift region 2 towards its right-hand end (as shown in FIG. 1) and an ionization or reaction region 3 towards its opposite left-hand end (as shown in FIG. 1).

An inlet conduit 4 opens at one end 5 to air or another source of gas or vapor to be sampled and analyzed. Air or gas is drawn through the conduit 4 by means of a pump 6 connected at the opposite end of the inlet conduit 4. At some point along the conduit a capillary passage 7 communicates between the conduit 4 and the interior of the reaction region 3 so that molecules of interest can pass from the conduit 4 into the reaction region 3. There are various other conventional arrangements by which substances can be admitted to the apparatus, such as utilizing a pin-hole, a membrane, or other similar apparatus. A pressure pulser 8, which may be an electromagnetic transducer similar to a loudspeaker, is connected to the housing 1 in the manner described in U.S. Pat. No. 6,073,498, to Taylor et al., which is hereby incorporated herein by reference. The pressure pulser is operated intermittently, momentarily to reduce pressure in the housing 1 and hence draw sample vapor or gas into the reaction region 3 as a bolus. A preconcentrator 9 may be included in the inlet conduit 4 or in the capillary passage 7 into the apparatus itself.

The reaction region 3 contains apparatus to ionize molecules of the analyte substance, such as a corona discharge point 10, at a high potential. The reaction region 3 and the drift region 2 are both at atmospheric pressure or just slightly below atmospheric pressure. The reaction region 3 and the drift region 2 may be separated from one another by an optional, conventional, electrostatic shutter 11 such as a Bradbury Nielson gate by which the flow of ions into the drift region 2 may be controlled. The drift region 2 has a series of pairs of electrodes 12 on opposite sides thereof which are longitudinally spaced from one another along the length of the drift region 2. A voltage supply 13 applies a voltage to each electrode pair 12, which voltage increases from the left to the right along the length of the drift region (as shown in FIG. 1) so that ions passed by the electrostatic shutter 11 are subject to a voltage gradient, which draws them along the length of the drift region 2. A collector plate 14 mounted at the far, right-hand end of the drift region 2 (as shown in FIG. 1) collects ions after passage along the drift region 2. The charge produced by each ion when it impacts the collector plate 14 is supplied as an electrical signal to a processor unit 15. The processor unit 15 analyzes the signals to produce spectra representative of the mobility of the different ions detected and supplies these to a display or other utilization apparatus 16.

As in a conventional IMS apparatus, a gas flow system 20 provides a flow of clean dry air along the inside of the housing 1 against the flow of the ions. The gas flow system includes a pump 21 with molecular sieve inlet and outlet filters 22 and 23 respectively located at its inlet and outlet. The inlet filter 22 connects with an inlet pipe 24, which opens into the housing 1 towards the inlet end of the reaction region 3 (shown on the left end in FIG. 1). The outlet filter 23 connects with an outlet pipe 25, which opens into the housing 1 towards the downstream end of the drift region 2 (shown on the right end in FIG. 1). The pump 21 operates to draw gas from the reaction region 3 so that it flows through the first filter 22, the pump 21, and the second filter 23 before flowing back into the housing 1 at the right-most end of the drift region 2 (as shown in FIG. 1).

The apparatus differs from conventional IMS apparatus. The apparatus of the present invention is arranged so that initially the gas flow system 20 supplies clean dry gas to the housing 1 before a sample gas or vapor is admitted. Just prior to triggering the pressure pulser 8 to introduce a bolus of the sample gas or vapor, the gas flow to the housing 1, and in particular to the reaction region 3, is reduced to zero or near zero by turning off the pump 21. The pressure pulser 8 is then triggered momentarily to inject a sample of analyte gas or vapor into the reaction region 3. Alternatively, the pressure pulser 8 could be dispensed with and sample gas or vapor just allowed to diffuse into the reaction region 3. Ions are produced continuously by the corona discharge point 10 from what is a substantially stationary sample cloud, which has a considerably increased residence time compared with conventional apparatus having a continuous gas flow. This enables the processor unit 15 to produce continuous ion mobility spectra. The ionization process does not significantly deplete the sample gas or vapor so a much longer average of ion mobility spectra can be acquired. This increases the signal-to-noise ratio. Just before the next analysis is required, the pump 21 is restarted to drive clean dry air through the apparatus and flush out the previous sample in the reaction region 3.

Figure 2:
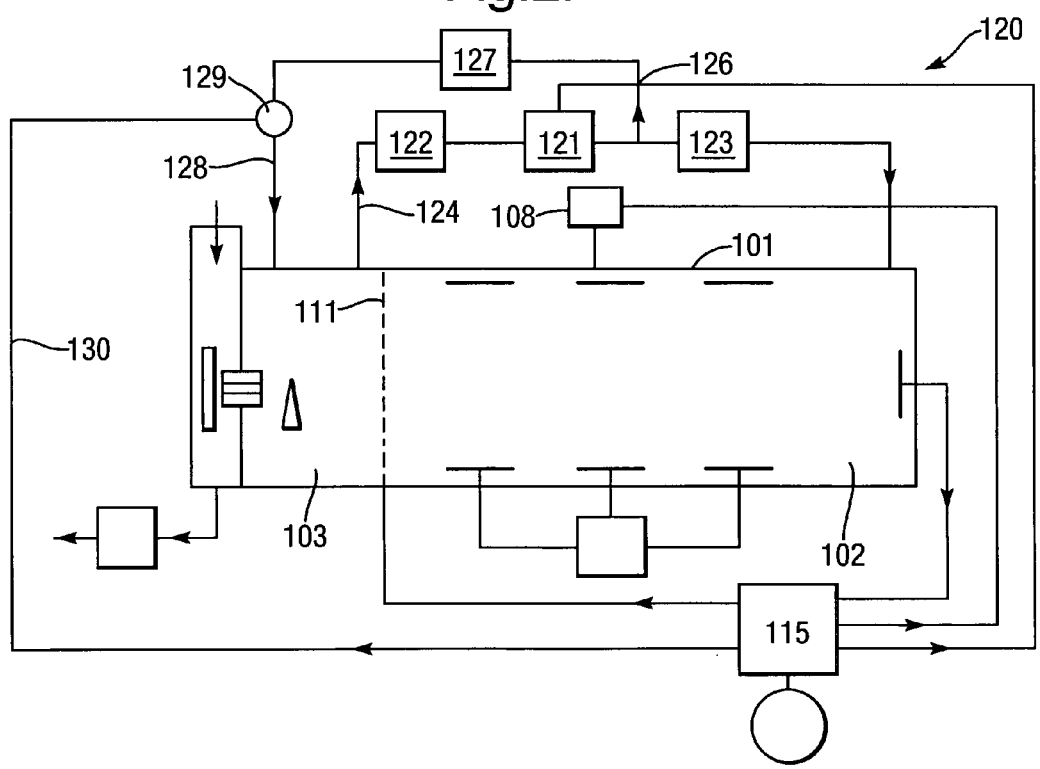
FIG. 2 shows alternative detection apparatus schematically.

It is not essential to stop gas flow through the entire housing 1; rather, it is only necessary to stop or substantially reduce gas flow through the reaction region 3 in order to increase the residence time during which the sample gas or vapor is subject to ionization. Some IMS apparatus have separate gas flow paths in the drift region and the reaction region. An IMS apparatus of this kind that is adapted to the present invention is shown in FIG. 2, where equivalent items to those in FIG. 1 are given the same reference numerals with the addition of 100. It can be seen that the inlet pipe 124 that is connected with a first filter 122 is located towards the right-most, downstream end of the reaction region 103 close to the electrostatic shutter 111. A spur pipe 126 forms a part of a secondary circuit and connects between the outlet of the pump 121 and a second filter 123. The spur pipe 126 extends to the inlet of a third molecular sieve filter 127. The outlet of the third filter 127 connects to a secondary outlet pipe 128, which opens into the housing 101 via a valve 129, with the opening of the secondary outlet pipe 128 into the housing 101 being located toward the left-hand end of the reaction region 103 (as shown in FIG. 2). The valve 129 is controlled electrically by the processor unit 115 via a cable 130. In this arrangement, the pump 121 operates continuously so that clean air flows in at the collector end of the drift region 102 and flows out close to the electrostatic shutter 111 at the downstream end of the reaction region 103. When the processor 115 opens the valve 129, gas will also flow via the spur pipe 126, the third filter 127, and the secondary outlet pipe 128 into the reaction region 103. This gas will flow to the right and will pass out of the region 103 via the outlet pipe 124. When a sample is to be admitted, the processor 115 closes the valve 129 to prevent gas entering the reaction region 103 via the pipe 128. Some gas will still flow through the reaction region 103 from the drift region 102, since this part of the gas flow is still operating, but this will be through a smaller portion of the reaction region 103 so the residence time for which the sample is exposed to the ionization effect will still be increased.

The present invention is particularly suited to detection arrangements where the sample is administered to the apparatus in the form of a bolus, such as by means of a preconcentrator inlet system. The invention is not necessarily confined to IMS apparatus, but may also be applicable to other detection apparatus.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A method of detecting substances in a detection apparatus having a reaction region arranged to provide ions to an analysis region where ion species produced in the reaction region are detected, the method comprising the steps of:
   selectively operating a gas flow system to supply a flow of clean gas through the reaction region;
   momentarily admitting an analyte gas or vapor to the reaction region while reducing the flow of clean gas through the reaction region substantially to zero just prior to momentarily admitting the analyte gas or vapor to the reaction region such that the residence time of the analyte gas or vapor in the reaction region is increased; and
   subsequently increasing the flow of clean gas through the reaction region.

2. The method defined in claim 1, wherein the step of momentarily admitting an analyte gas or vapor to the reaction region comprises:
   reducing pressure in the detection apparatus momentarily by operating a pressure pulser.

3. The method defined in claim 1, wherein the step of momentarily admitting an analyte gas or vapor to the reaction region is facilitated by an inlet apparatus comprising a preconcentrator.

4. The method defined in claim 1, wherein the gas flow system is operated to flow the clean gas along substantially the entire length of the detection apparatus.

5. The method defined in claim 1, wherein the step of operating the gas flow system to supply a flow of clean gas through the reaction region comprises:
   operating a first gas flow circuit connected between an end of the detection apparatus remote from an inlet thereto and an end of the reaction region remote from the inlet;
   operating a secondary gas flow circuit extending from an end of the reaction region adjacent the inlet to the end of the reaction region remote from the inlet; and
   closing the secondary gas flow circuit when an analyte gas or vapor is to be admitted.

6. The method defined in claim 1, additionally comprising:
   operatively connecting a processor unit to operate the gas flow system and an apparatus for momentarily admitting the analyte gas or vapor to the reaction region;
   activating the processor unit to operate the gas flow system and the apparatus for momentarily admitting the analyte gas or vapor to reduce the flow of clean gas through the reaction region substantially to zero just prior to momentarily admitting the analyte gas or vapor to the reaction region such that the residence time of the analyte gas or vapor in the reaction region is increased; and
   subsequently activating the processor unit to operate the gas flow system to increase the flow of clean gas through the reaction region.

7. The method defined in claim 1, additionally comprising:
   selectively controlling the flow of ions from the reaction region to the analysis region with an electrostatic shutter.

8. The method defined in claim 1, additionally comprising:
   ionizing molecules of the analyte gas or vapor that has been admitted to the reaction region.

9. The method defined in claim 1, additionally comprising:
   establishing an electrical field in the analysis region which draws ions located in the analysis region in a direction from the reaction region to the analysis region.

10. The method defined in claim 1, additionally comprising:
    collecting ions passing to the end of the analysis region opposite the end of the analysis region closest to the reaction region and providing an output indicative of the ions detected by the collector plate.

11. A method of detecting substances comprising the steps of:
momentarily admitting a sample of a substance into a reaction chamber;
flowing a gas through the reaction chamber;
producing ions from the sample;
passing ions from the reaction chamber to a collector for detection; and
periodically reducing the flow of gas through the reaction chamber thereby to prolong the time during which the sample is present in the reaction chamber.

12. The method defined in claim 11, wherein the ions are passed from the reaction chamber to the collector via a drift region having a voltage gradient along its length.

13. The method defined in claim 11, wherein the flow of gas through the reaction chamber is reduced substantially immediately prior to admitting the sample of a substance into a reaction chamber such that the residence time of the analyte gas or vapor in the reaction region is increased, and wherein the flow of gas through the reaction chamber is subsequently increased.

14. A method of detecting substances in a detection apparatus having a first end at which an analyte gas or vapor will be admitted to the housing and a second end opposite the first end, the method comprising the steps of:
selectively admitting an analyte gas or vapor to a reaction region located in the detection apparatus adjacent the first end thereof, a drift region being located in the detection apparatus between the reaction region and the second end of the detection apparatus;
selectively operating a gas flow system to supply a flow of clean gas at least through the reaction region;
coordinating the operation of the admitting step and the operating step to operate the gas flow system to reduce the flow of clean gas through the reaction region substantially immediately prior to admitting the analyte gas or vapor to the reaction region such that the residence time of the analyte gas or vapor in the reaction region may be increased; and
subsequently increasing the flow of clean gas through the reaction region.

15. The method defined in claim 14, wherein the gas flow system is operated to flow the clean gas along substantially the entire length of the detection apparatus.

16. The method defined in claim 14, wherein the step of operating the gas flow system to supply a flow of clean gas through the reaction region comprises:
operating a first gas flow circuit having a first inlet in the detection apparatus located near the second end of the detection apparatus and a first outlet in the detection apparatus located at an end of the reaction region remote from the first end of the detection apparatus;
operating a secondary gas flow circuit having a second inlet in the detection apparatus located near the first end of the detection apparatus and a second outlet in the detection apparatus located at an end of the reaction region remote from the first end of the detection apparatus.

17. The method defined in claim 16, wherein the first outlet in the housing and the second outlet in the housing together comprise a single outlet from the housing.

18. The method defined in claim 16, wherein the steps of reducing the flow of clean gas through the reaction region substantially and subsequently increasing the flow of clean gas through the reaction region comprise:
reducing the flow of clean gas through the secondary gas flow circuit; and
subsequently increasing the flow of clean gas through the secondary gas flow circuit.

19. The method defined in claim 16, additionally comprising:
establishing an electrical field in an analysis region located intermediate the reaction region and the second end of the detection apparatus, wherein the electrical field in the analysis region draws ions located in the analysis region in a direction from the reaction region to the analysis region.

20. The method defined in claim 19, additionally comprising:
selectively controlling the flow of ions from the reaction region to the analysis region.

* * * * *